(12) United States Patent
Lechot et al.

(10) Patent No.: US 7,749,227 B2
(45) Date of Patent: Jul. 6, 2010

(54) PRECISION ASSEMBLEABLE SURGICAL TOOL HANDLE WITH LIMITED-PLAY INTERCONNECT MECHANISM

(75) Inventors: André Lechot, Orvin (CH); Thomas Lamadon, Les Verrières-de-Joux (FR)

(73) Assignee: Greatbatch Medical S.A., Clarence, NY (US)

(*) Notice: Subject to any disclaimer, the term of this patent is extended or adjusted under 35 U.S.C. 154(b) by 593 days.

(21) Appl. No.: 11/536,792

(22) Filed: Sep. 29, 2006

(65) Prior Publication Data
US 2008/0058804 A1    Mar. 6, 2008

(51) Int. Cl.
*A61B 17/00* (2006.01)
*A61B 17/32* (2006.01)
*A61B 17/56* (2006.01)
*A61F 2/30* (2006.01)
*A61F 2/32* (2006.01)
*A61F 2/34* (2006.01)
*A61F 2/36* (2006.01)

(52) U.S. Cl. ............... 606/80; 606/79; 606/81; 606/85; 606/86; 606/87; 606/88; 606/89; 606/62; 606/67; 606/99; 606/104; 606/180

(58) Field of Classification Search ............ 606/79–81, 606/85–89, 62, 67, 99, 104, 180
See application file for complete search history.

(56) References Cited

U.S. PATENT DOCUMENTS

| | | | |
|---|---|---|---|
| 2,093,682 A | 9/1937 | Levy | |
| 4,716,894 A * | 1/1988 | Lazzeri et al. | 606/91 |
| 5,176,711 A | 1/1993 | Grimes | |
| 5,697,158 A | 12/1997 | Klinzing et al. | |
| 5,814,049 A | 9/1998 | Pratt et al. | |
| 5,924,978 A * | 7/1999 | Koeda et al. | 600/178 |
| 6,096,042 A | 8/2000 | Herbert | |
| 6,860,668 B2 * | 3/2005 | Ibrahim et al. | 403/56 |
| 2002/0002365 A1* | 1/2002 | Lechot | 606/1 |
| 2005/0240192 A1* | 10/2005 | Lechot et al. | 606/80 |

FOREIGN PATENT DOCUMENTS

| | | |
|---|---|---|
| DE | 25 47 969 | 4/1977 |
| DE | 38 28 478 | 5/1989 |
| EP | 0 261 260 | 3/1988 |
| EP | 1 074 225 | 2/2001 |
| WO | WO 03/065906 | 8/2003 |
| WO | WO 03/092513 | 11/2003 |

* cited by examiner

*Primary Examiner*—Thomas C Barrett
*Assistant Examiner*—Sameh Boles
(74) *Attorney, Agent, or Firm*—Michael F. Scalise

(57) ABSTRACT

A precision adjustable surgical tool holder/driver is provided which is easily disassembled for cleaning and precisely reassembled. The holder/driver has a positionable handle allowing adjustment of the position of the handle about the spindle of the holder to enable the "handedness" of the holder to be changed in order to accommodate a user while operating from the left or right side of the patient, standing behind or in-front of the patient, or for use in different surgical methods. The holder/driver includes a "limited-play" capture mechanism, which connects the drive end of the housing to its locking sleeve via a limited-play locking device. The limited-play locking device utilizes a disengageable, precision fitted bayonet pin and seat combination in part to accomplish the precision reassembly feature of the present invention.

25 Claims, 16 Drawing Sheets

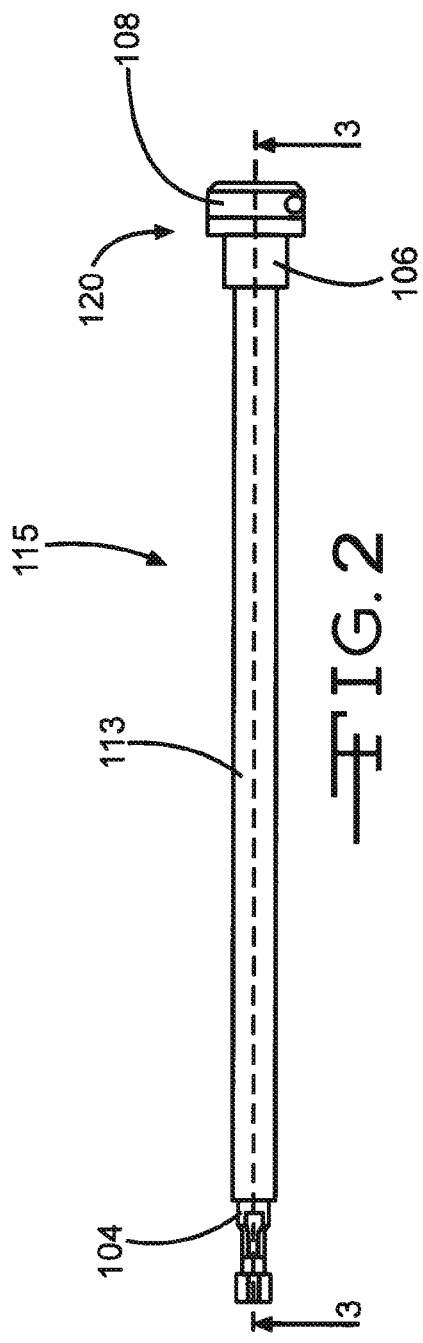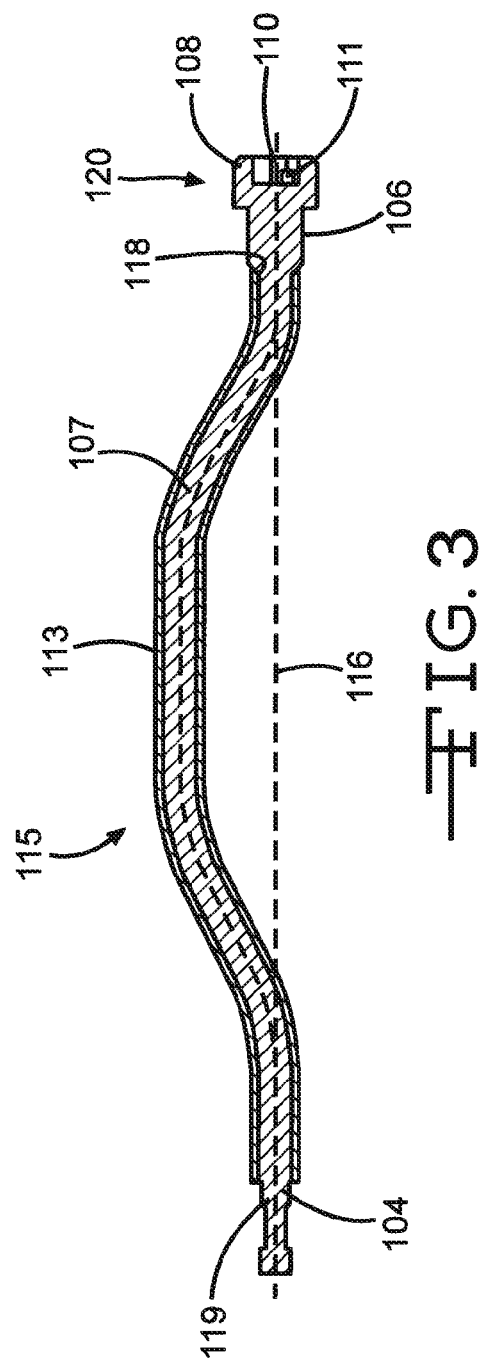

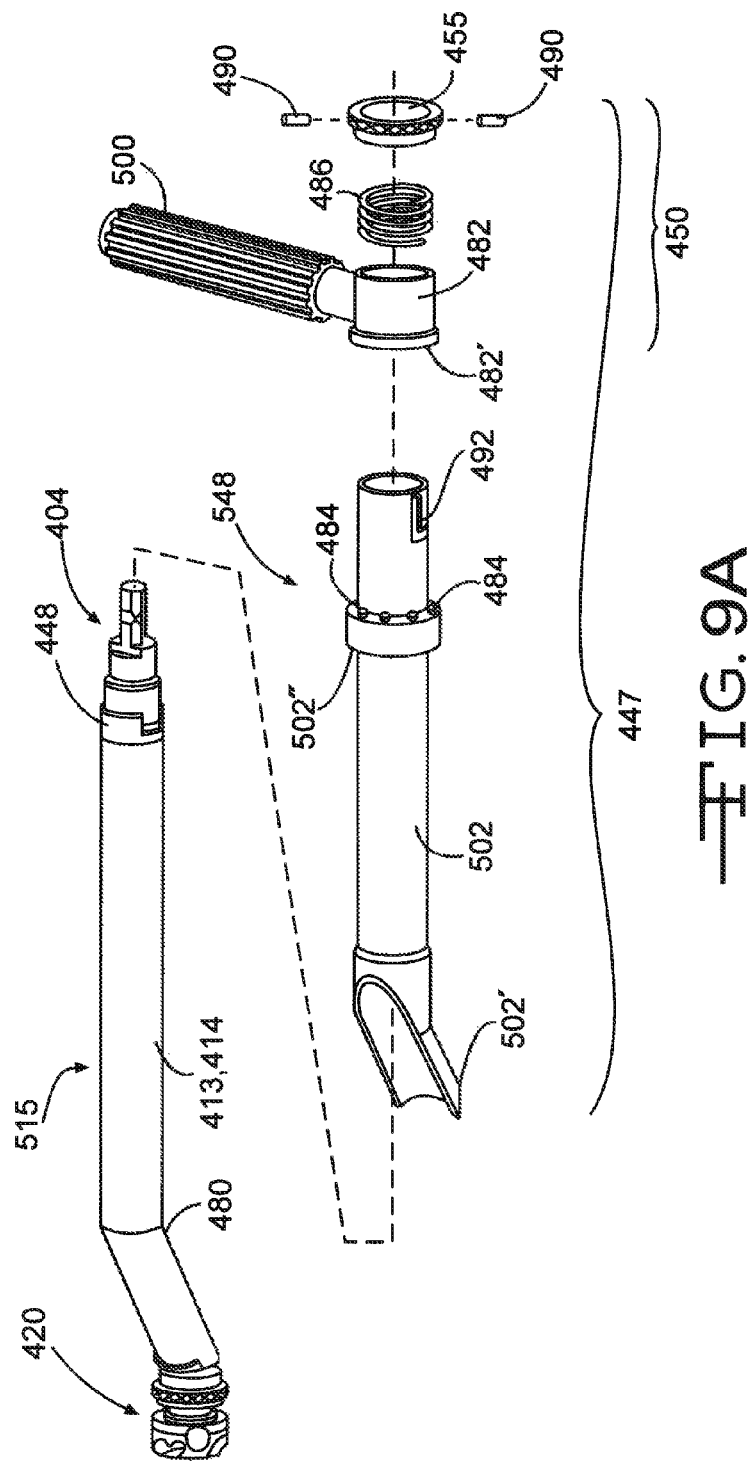

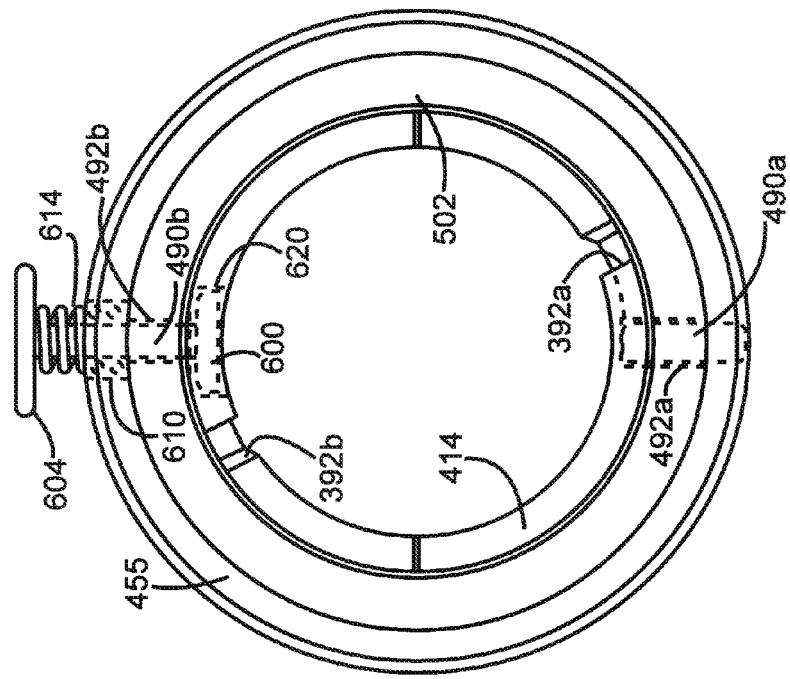
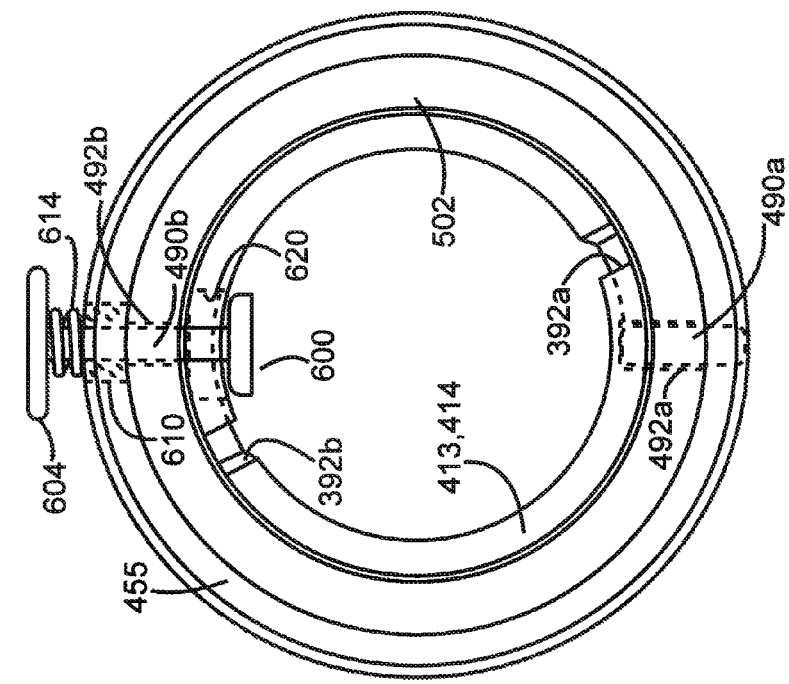

Step 1.1 : Assembly
Hold the knurled ring between the index finger and thumb.
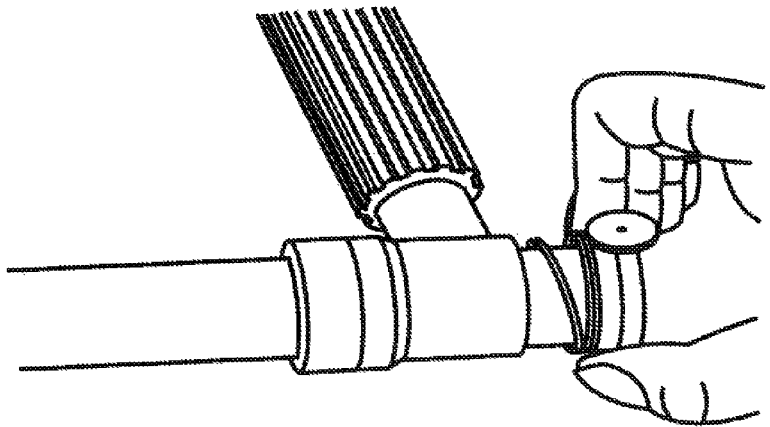
Step 1.2 : Assembly
Press inward.
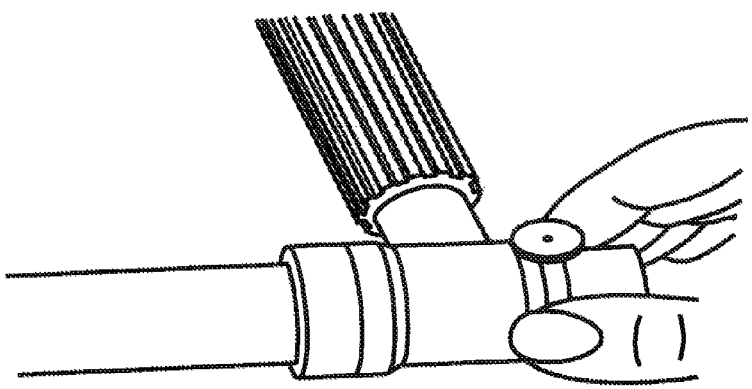
Step 1.3 : Assembly
Twist counter-clockwise until the button clicks into place.
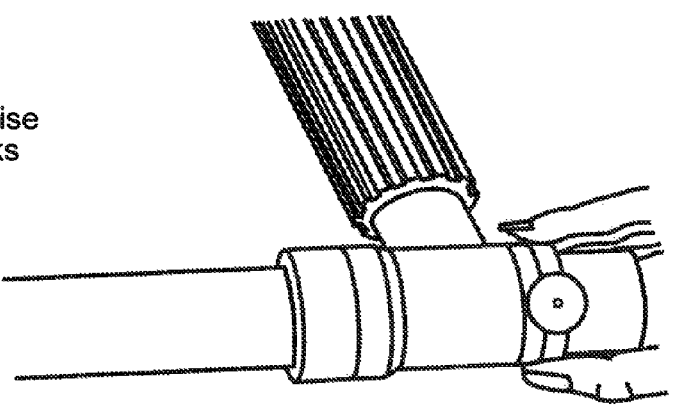
FIG. 13A

Step 1.1 : Disassembly
Press the button.
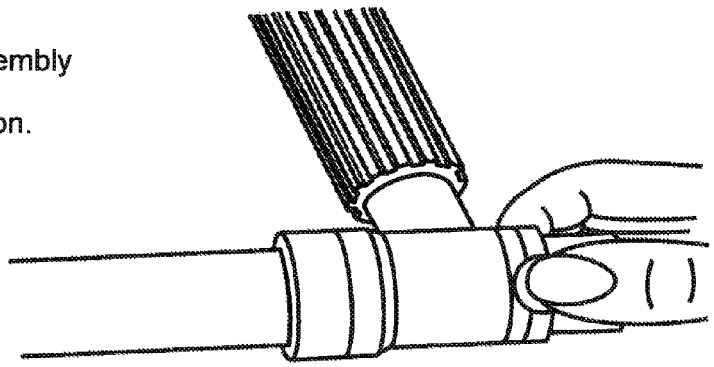
Step 1.2 : Disassembly
Twist clockwise.
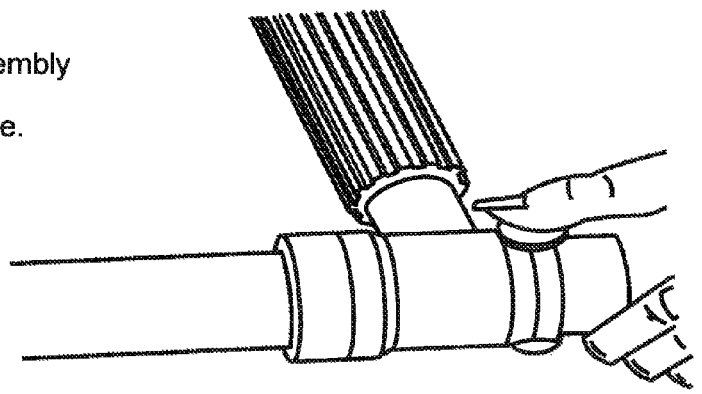
Step 1.3 : Disassembly
Release mechanism to open.
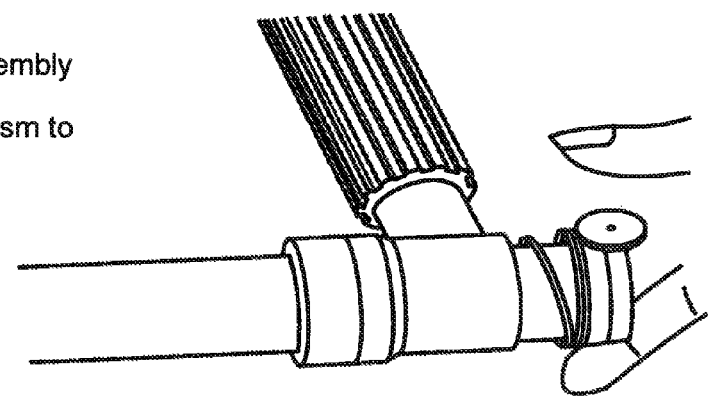
FIG. 13B

PRECISION ASSEMBLEABLE SURGICAL TOOL HANDLE WITH LIMITED-PLAY INTERCONNECT MECHANISM

CROSS REFERENCE TO RELATED APPLICATIONS

The present application claims the benefit of prior filed U.S. Provisional Patent Application Ser. No. 60/765,692 filed 6 Feb. 2006, to which the present application is a regular U.S. national application, and of prior PCT application No. PCT/1B03/01725, filed 28 Apr. 2003.

FIELD OF THE INVENTION

The present invention is in the field of surgical tools and accessories for performing orthopedic surgery. More particularly, the present invention relates to handles tool holders useful in orthopedic surgical procedures, the handles/holders being precision surgical tool handles with a limited-play interconnect mechanism.

BACKGROUND

Complicated mechanical devices have crevices and recesses that are difficult, if not almost impossible, to clean with ease. Devices that are not properly cleaned and sterilized contribute to the risk of disease transfer from patient to patient following the emergence of certain "prions" that are not killed by normal hospital sterilization and need to be physically removed by washing/rinsing. Although surgical tool handles are known in the field (see PCT/GB2002/02934 to Chana, incorporated herein by reference), those using "J-slot" (bayonet type) interconnect mechanisms can be subject to play at the interconnections. It would be beneficial in the field to have an interconnect mechanism that has the advantages of the existing "J-slot" interconnect mechanisms, but is less subject to play in the connection.

SUMMARY

The present invention comprises an adjustable reamer spindle designed to aid a surgeon to better control the instrument. Adjustment of the position of the handle axis of the spindle enables the axis through the palm/grip of each hand to change in order to provide maximum control in different orientations. The adjustment is desirable in order to accommodate operating on the left or right side of the patient standing behind or in front of the patient, or the use of a different surgical approach. Further, adjustment is important to accommodate the differing needs of surgeons who are naturally left or right handed. In such an instrument that is intended for either right or left handed use, or both CW and CCW rotation in use, it is important to provide an interconnect mechanism that minimizes axial play when used with either hand, or both CW and CCW rotation.

The present invention comprises a precision surgical tool holder/handle which is assemblable over and over again to precise radial, axial and length relationships of its components. The precision tool driver has a precision spindle housing in which a drive train is retained. The drive chain has a drive attachment end connectable to a means for rotating the drive chain, and a tool holder end connectable to a surgical tool head. The tool holder end has an axis of rotation relative to the spindle housing, and an axial displacement aspect relative to a tool end of the spindle housing. The axis of rotation is precisely defined by the relationship between the spindle housing and the drive chain at the tool holder end of the drive chain. The axial displacement aspect is definable as the distance between the tool end of the spindle housing and the tool holder end.

The handle has a fitted locking sleeve which closely receives the spindle housing and drive chain combination. The locking sleeve has a sleeve axis which is disposed precisely parallel to the axis of rotation when the spindle housing and drive chain combination is received by the locking sleeve. The locking sleeve has a mating means interfacing with the spindle housing which precisely fixes a radial aspect relationship between the spindle housing and the locking sleeve when the spindle housing is received by the locking sleeve.

A precision locking device is retained on the locking sleeve. The locking device has an annular collar slideable on the drive end of the locking sleeve, between a sleeve shoulder and a collar ring. The annular collar has a handle attached to it, a collar axis, and an attachment point at which the handle is fixed to the annular collar. Typically, the attachment point is disposed on a radius of the collar axis. The collar ring is releaseably engageable to bias the collar against the sleeve shoulder at a precision radial interface to precisely fix the radial aspect relationship between the attachment point and the collar radius.

A releaseable capture mechanism is provided to integrate the assemblies of the present invention into a working whole. The capture mechanism is embodied in part in each of: the spindle housing/drive chain, locking sleeve and locking device assemblies. The capture mechanism comprises a precision bayonet-type connection cooperatively involving the spindle housing, the locking sleeve and the locking device. The precision bayonet connection includes the collar ring which has an internal surface from which at least two bayonet pins extend radially inward. The bayonet pins pass through retainer slots disposed in the locking sleeve, as described elsewhere. When the locking sleeve assembly is slid over the spindle housing/drive chain assembly, the bayonet pins are received into bayonet slots on the spindle housing corresponding to the retainer slots on the locking sleeve. The bayonet slots are disposed to releaseably engage the bayonet pins. At least one of the bayonet slots has a precision pin seat to engage a precision bayonet pin head on its corresponding bayonet pin.

When the capture mechanism is engaged, the spindle housing/drive chain assembly, the fitted locking sleeve assembly and the locking device all cooperate through the capture mechanism to provide the present precision surgical tool driver repeatably assembleable to precise radial, axial and length aspect relationships of its components and the device overall.

The releaseable capture mechanism has a precision bayonet-type connection between the spindle housing, the locking sleeve and the locking device. The collar ring has an internal surface from which at least two bayonet pins extend radially inward, and pass through retainer slots disposed in the end of the locking sleeve. The retainer slots correspond to bayonet slots in the spindle housing. The bayonet slots are disposed to releaseably engage the bayonet pins. At least one of the bayonet slots has a precision pin seat to engaging a precision bayonet pin head on its corresponding precision bayonet pin.

The spindle housing and drive chain combination, the fitted locking sleeve, the locking device and the capture mechanism all cooperating to provide the present repeatably assembleable precision surgical tool driver.

BRIEF DESCRIPTION OF THE DRAWINGS

FIG. 2 is a top view of the reamer spindle of the present invention.

FIG. 3 is a section view taken along line 3-3 shown in FIG. 2.

FIG. 9A is an exploded view of the alternate embodiment of FIG. 8.

FIGS. 11A and 11B are end-on views of the drive ends of the spindle housing and the locking sleeve assembly, illustrating a limited play interconnection between the housing and the sleeve, with the fitted bayonet pin disengaged from its seat (A), and engaged in its seat (B).

FIGS. 13A and 13B are instructional illustrations of a manner in which the locking device can be operated.

DETAILED DESCRIPTION OF THE INVENTION

Figure 1:
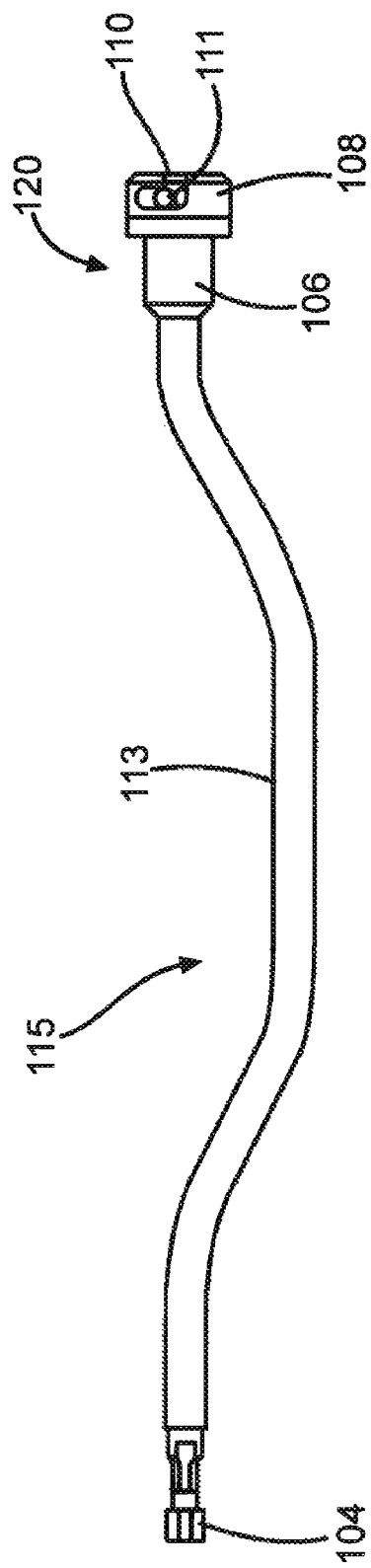
FIG. 1 is a side view of the reamer spindle of the present invention.

Referring now to the drawings, the details of embodiments of the present invention are graphically and schematically illustrated. Like elements in the drawings are represented by like numbers, and any similar elements are represented by like numbers with a different lower case letter suffix.

In one embodiment, the present invention comprises a reamer spindle 115 as shown in FIGS. 1-3, and 5. The reamer spindle 115 has a housing 113 containing a drive shaft 107. The drive shaft 107 has a proximal end drive fitting 104 adapted to be attachable to a controllable motive source (not shown). The motive source is provided to rotate the drive shaft 107 inside the reamer spindle 115. The drive shaft 107 has a distal end tool holder fitting 120 for holding a tool head 10, such as a reamer in the embodiment illustrated (see FIG. 5).

The drive fitting 104 and the tool holding fitting 120 are disposed to mate with a complimentary fitting on a motive source and a tool head 10, respectively.

In the embodiments illustrated, the tool holding fitting 120 is illustrated as comprising a complementary part of a bayonet-type connection mechanism. However, as further illustrated below, a complementary part of a bayonet-type mechanism can be used at other connections on a tool spindle 115. The tool holding fitting 120 had a slide 106 carrying a pin 111. The pin 111 works cooperatively with the catch 110 located in the head 108 to form the bayonet for capturing the complementary fitting on a tool head 10, while allowing easy release. The tool heads 10 (reamers in this embodiment) selected for use with the reamer spindle 115 can be shaped and sized for cutting different osseous sites within the body. It is widely known that reamers can be designed to cut the patella in a knee or the glenoid in a shoulder or the socket 45 in an acetabulum 40 as shown in FIGS. 4 and 5.

Figure 4:
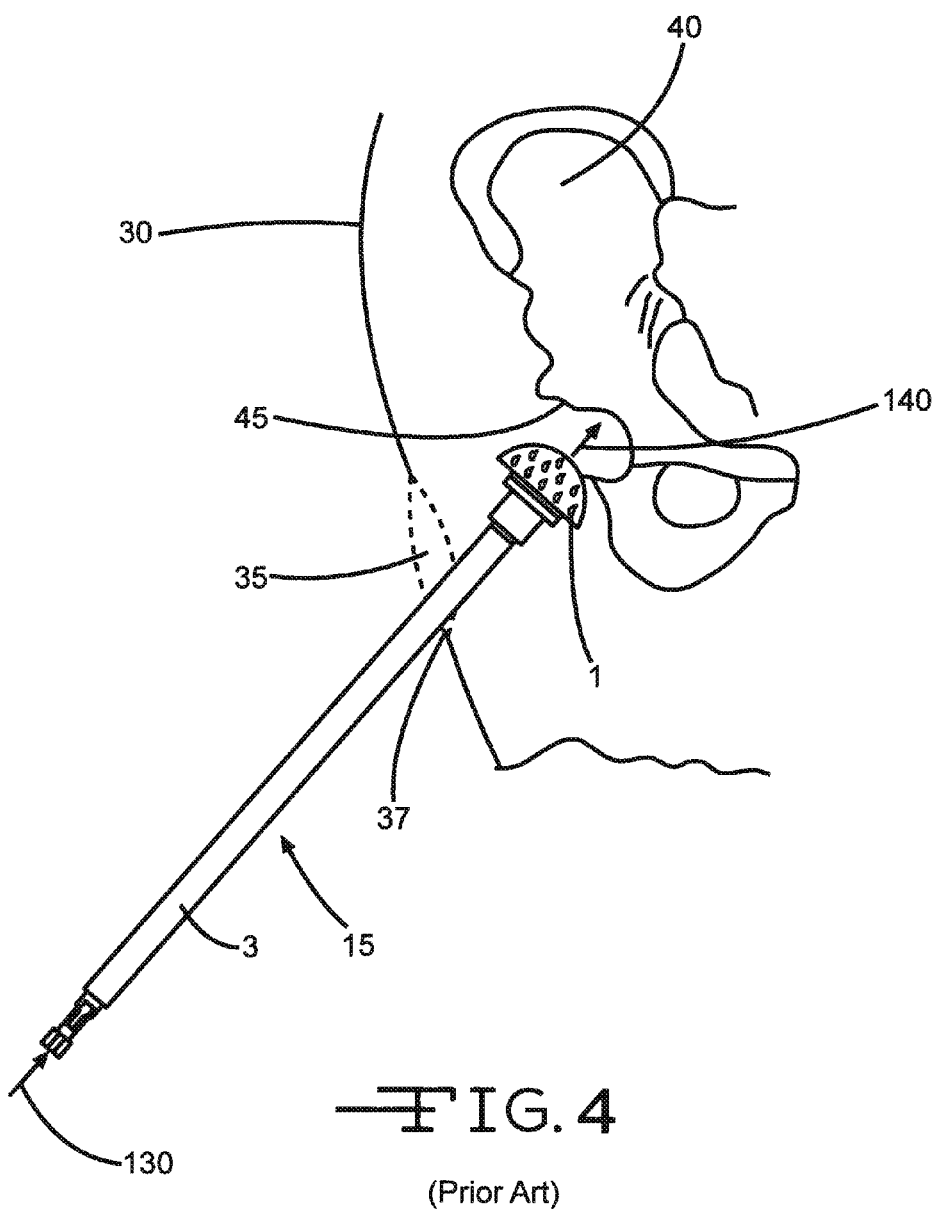
FIG. 4 is a plan view showing a traditional reamer spindle of the prior art being used in a minimally invasive approach for reaming the acetabular socket.
Figure 5:
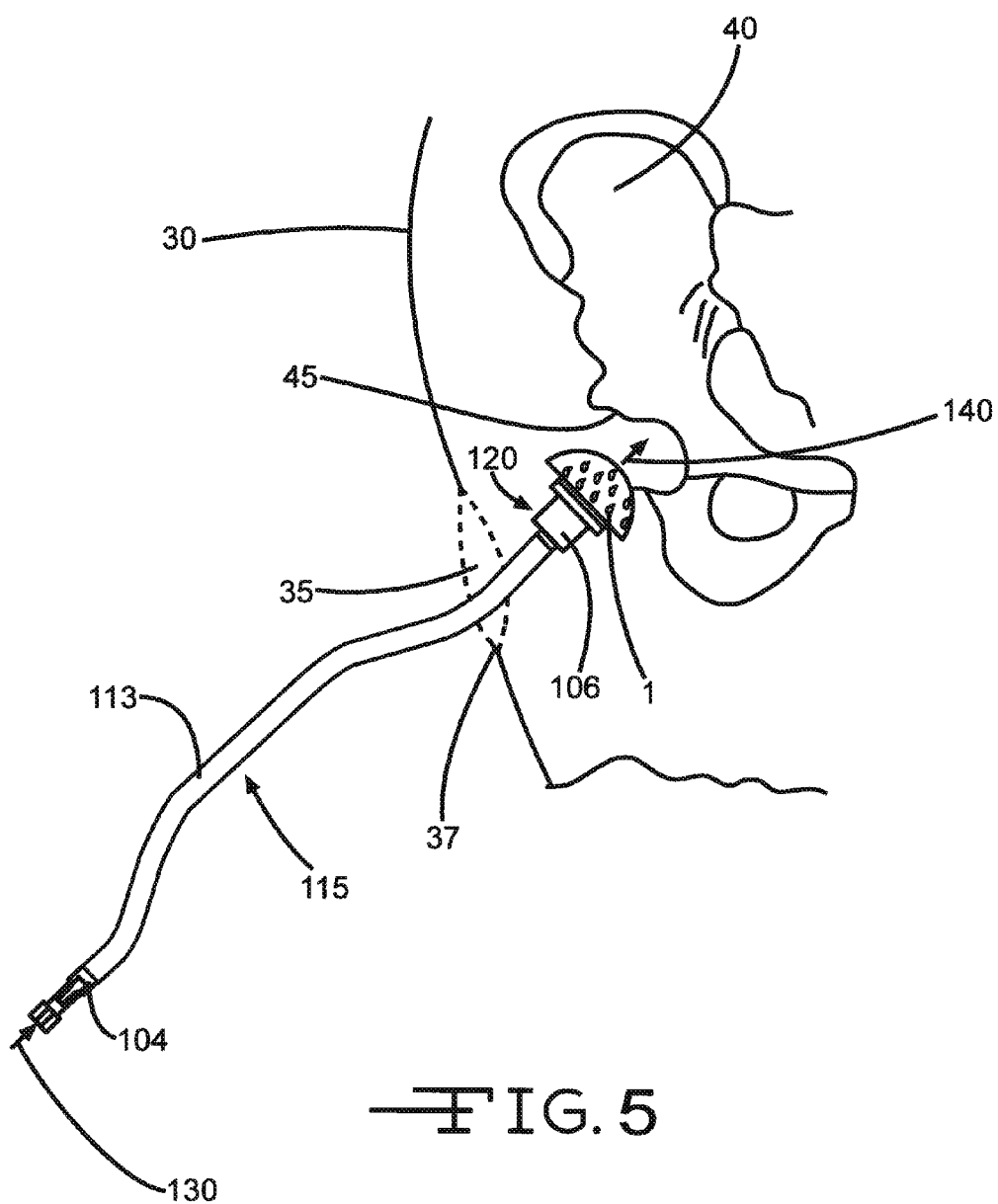
FIG. 5 is a plan view showing the reamer spindle of the present invention being used in a minimally invasive approach for reaming the acetabular socket.

Referring to FIGS. 4 and 5, the reamer spindle 115 of the present invention and the spindle 15 of the prior art invention are shown passing through a miniature incision 35 in the patient's skin 30. In prior art FIG. 4, the reamer spindle 15 is shown approaching the acetabulum 40 in a preferred orientation for reaming the socket 45. A difficulty with the prior art spindle 15 is that, as shown, the shaft 3 can impinge on the miniature incision 35 at edge 37 of the incision. The current surgical protocols are being pushed to the limits and the incision sizes are being reduced with the intent of increasing the patient's recovery speed. In some cases, surgeons are using a two-incision approach, one to reach the acetabulum and the other to reach the femur. Depending on the situation, either the one incision or the two incision technique can result in less trauma to the patient, thus requiring the instruments to be flexible and more optimally designed to make up for the lack of operating space.

The reamer 115 of FIG. 3 shows a present reamer spindle 115, which has a bent housing 113 containing the drive shaft 107. The drive shaft 107 can be selected from a variety of current torque transmitting mechanisms or devices including a Nickel Titanium shaft, a flexible round or flat wire wound cable, a series of gear driven shafts, or a series of shafts interconnected by universal joints. The drive shaft 107 can also be selected from any torque transmission mechanism or device deemed appropriate for the application, as selectable by one of ordinary skill in the art for practice in the present invention. As illustrated, the drive shaft 107 can be held to the housing 113 with an optional series of bearing surfaces 118 and 119 which keep the drive shaft 107 from bearing against/ riding on the inside of the housing 113, and can act as a shield to protect the inner housing from blood. Other means for holding the shaft to the housing would be acceptable. The most important feature of the drive shaft 107 is that it conforms to the selected housing 113 and sufficiently supplies torque to the tool head 10. In these examples, the housing 113 is hollow and maintains the drive end fitting 104 substantially collinear with the tool holder fitting 120 (see FIGS. 3 and 6), but as illustrated below, other configurations are intended as well.

Figure 6:
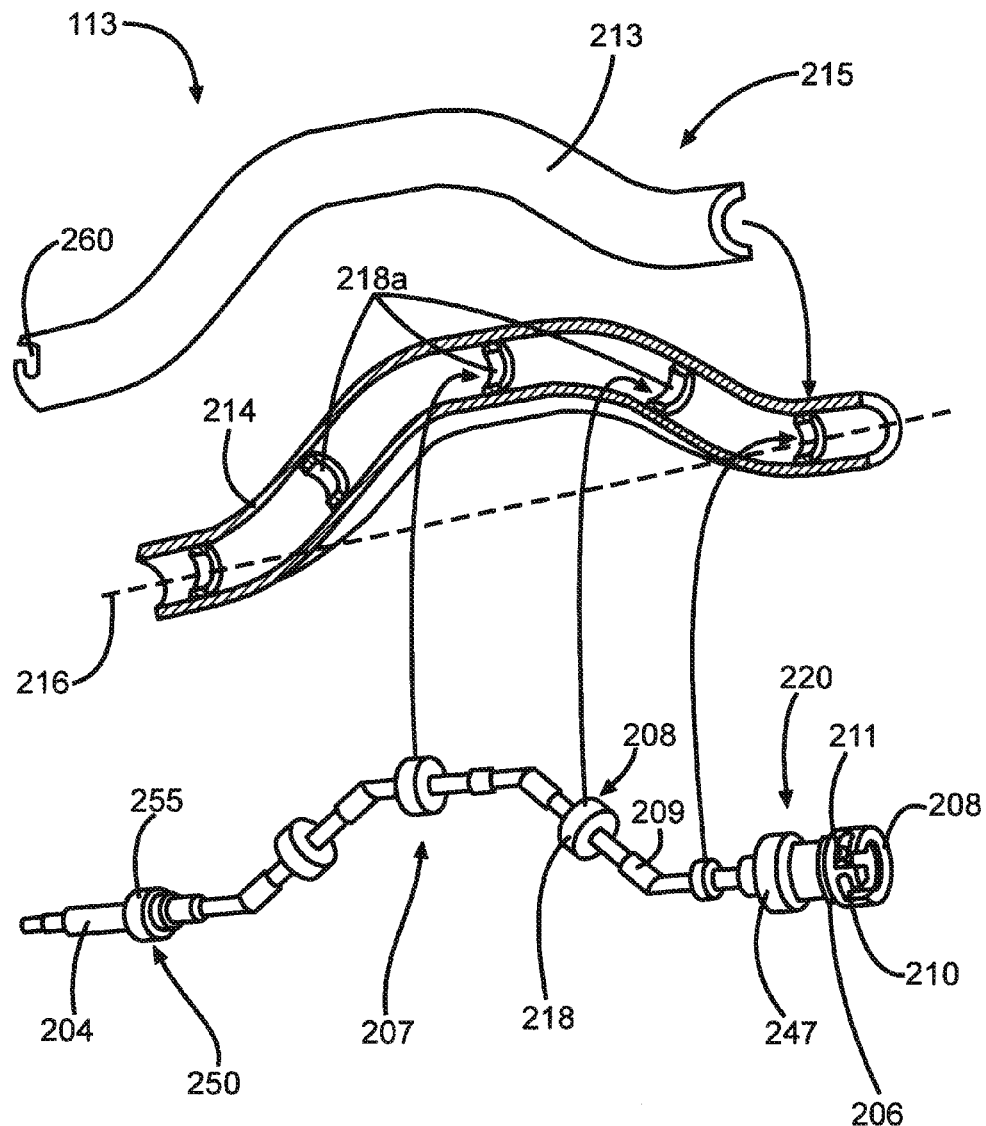
FIG. 6 is an exploded assembly of an alternative embodiment of the present invention.

Referring now to FIG. 6, an alternative embodiment is shown. Similar to FIGS. 1-3 and 5, the reamer spindle 215 has a housing 113 in two parts 213 and 214 containing a drive shaft 207. The drive shaft 207 has a proximal end drive fitting 204 adapted to be attachable to a controllable motive source (not shown). The motive source is provided to rotate the drive shaft 207 inside the reamer spindle 215. The drive shaft 707 has a distal end tool holder fitting 220 for holding a tool head 10. The drive fitting 204 and the tool holding fitting 220 are disposed to mate with a complementary fitting on a motive source and a tool head 10, respectively. The drive shaft 207 can be selected from a variety of current torque transmitting mechanisms or devices including a Nickel Titanium shaft, a flexible round or flat wire wound cable shaft, a series of gear driven shafts, or a series of linkages 208 interconnected by universal joints 209. The drive shaft 207 can also be selected from any torque transmission mechanism or device deemed appropriate for the application. In this embodiment, the shaft 207 is constructed from a series of linkages 208 containing universal joints 209 and bearing members 218 which rest against journey supports 218*a* in the housing parts 213 and 214.

The drive shaft 207 can be flexible substantially throughout its length, but, since it is not necessary to feed the drive shaft 207 into the housing 113, it is required to be flexible only along portions of its length received in curved portions of the housing 113. Along straight portions of its length, the drive shaft 207 can be rigid. Flexibility in drive shaft 207 is required only to allow its rotation within curved portions of the housing 113. As noted above, the drive shaft 207 can be conventional, wound-wire cable flexible along its length, and having one or more alternating layers wound in opposite directions. A protective, friction reducing sheath (not shown) can be provided on such a drive shaft. Other types of flexible drive shafts also can be used. Spaced bearing journals (not shown) and/or lubricant can be provided within outer shaft 50. That is to allow proper positioning of the drive shaft 56 in outer shaft 50, and to reduce resistance to rotation of drive shaft 56 within outer shaft 50.

The tool holder fitting 220 preferably comprise a complementary part of a bayonet-type mechanism with a slide 206 carrying a pin component 211. The pin 211 works cooperatively with the catch 210 located in the head 208 to form the bayonet for capturing different size reamers while allowing their easy release for size interchangeability and cleaning. The drive shaft 207 is set in housing parts 213 and 214, which are separable for cleaning.

Figure 7:
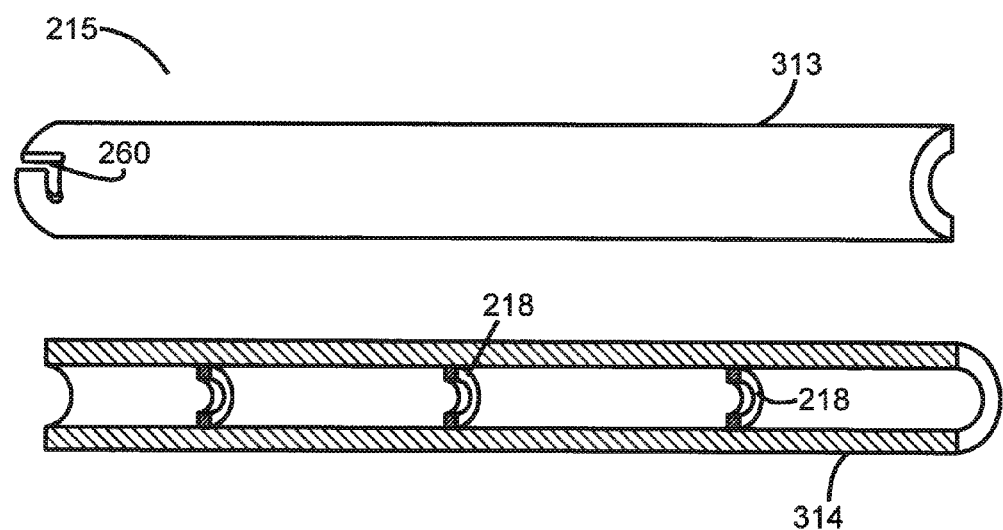
FIG. 7 is an alternative shape housing of the alternative embodiment shown in FIG. 6.

There are many ways of connecting the housing part 213 and 214 together. For example, the drive shaft 207 can include a capture mechanism 247 which is adapted to receive the front ends of the housing parts 213 and 214 aligning each with one another and encapsulating the drive shaft 107 to protect the patient's skin from contacting the torque transmitting shaft 207 during operation. Once the housing parts 213 and 214 are aligned, a locking mechanism 250 comprised of a ring 255 and a catch 260, which is located in the housing member 213, interact with one another to retain the housing parts 213 and 214 in a closed fashion. As with the embodiment described in FIGS. 1-3, and 5, it is preferable to have the drive end 204 substantially collinear with the holding mechanism 220 along axis 216. The housing parts 213 and 214 are shown preferably in FIG. 6 in a bent configuration. However, the reamer spindle 215 can embody a housing in two parts, wherein the housing parts 313 and 314 are straight and have no bend, as shown in FIG. 7.

Figure 8:
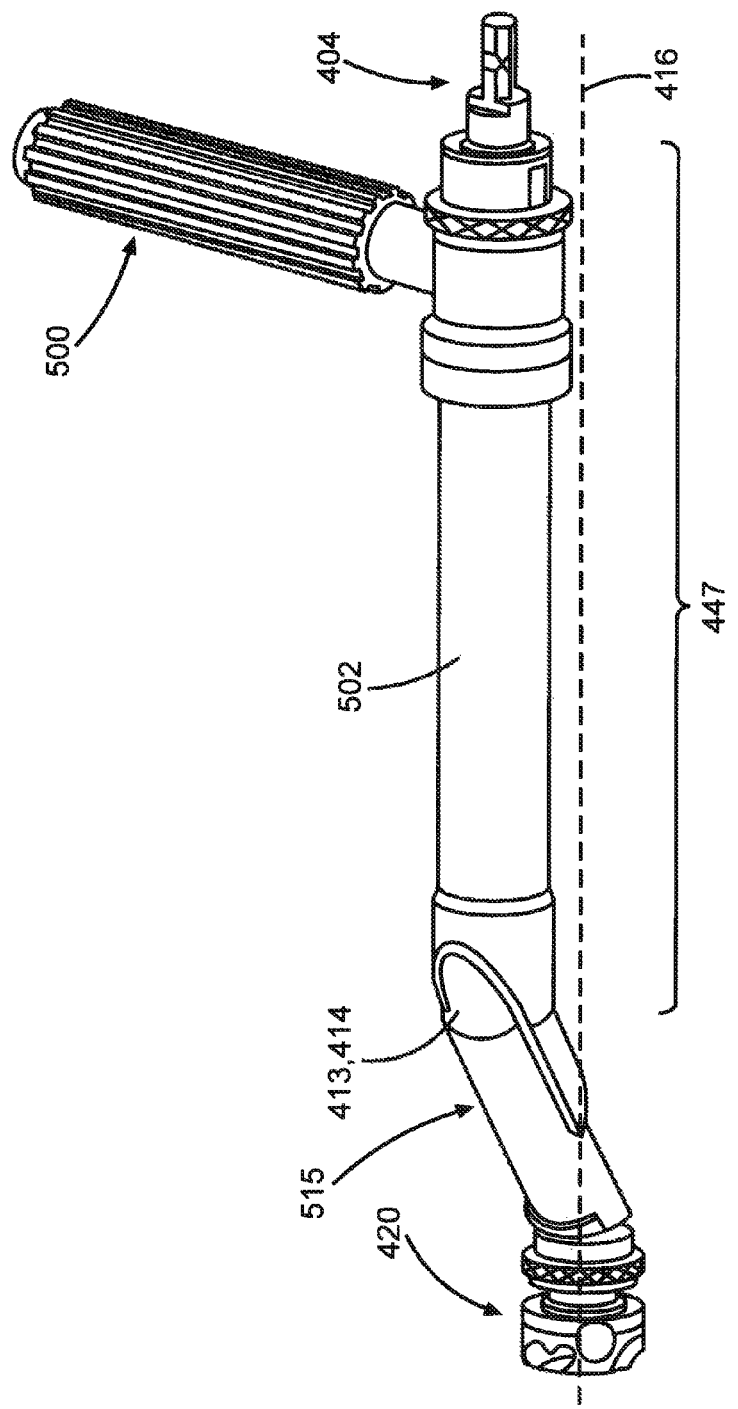
FIG. 8 is a perspective view of an alternate embodiment of the invention having a repositionable handle.

Referring now to FIGS. 8 et seq., alternatively, the drive end 404 is situated along an axis parallel to, but offset from, the axis 416 of the tool holder fitting 420. A bend 480 in the housing is optimally placed at a location to pass through the miniature incision (see FIG. 5) without impinging on the skin 30 at location 37 while still maintaining the same surgical protocol. The drive end fitting 404 and the tool holder fitting 420 have parallel axes, so that an inline force applied to the drive fitting 404 results in an axial force applied to the tool holder fitting 420. This allows the surgeon to maintain the existing surgical technique and accomplish the same result as when a prior reamer spindle 15 is used with its straight drive shaft 3 (see FIG. 4). Thus, the surgeon is able to apply a load directly along the path of reaming.

Figure 9B:
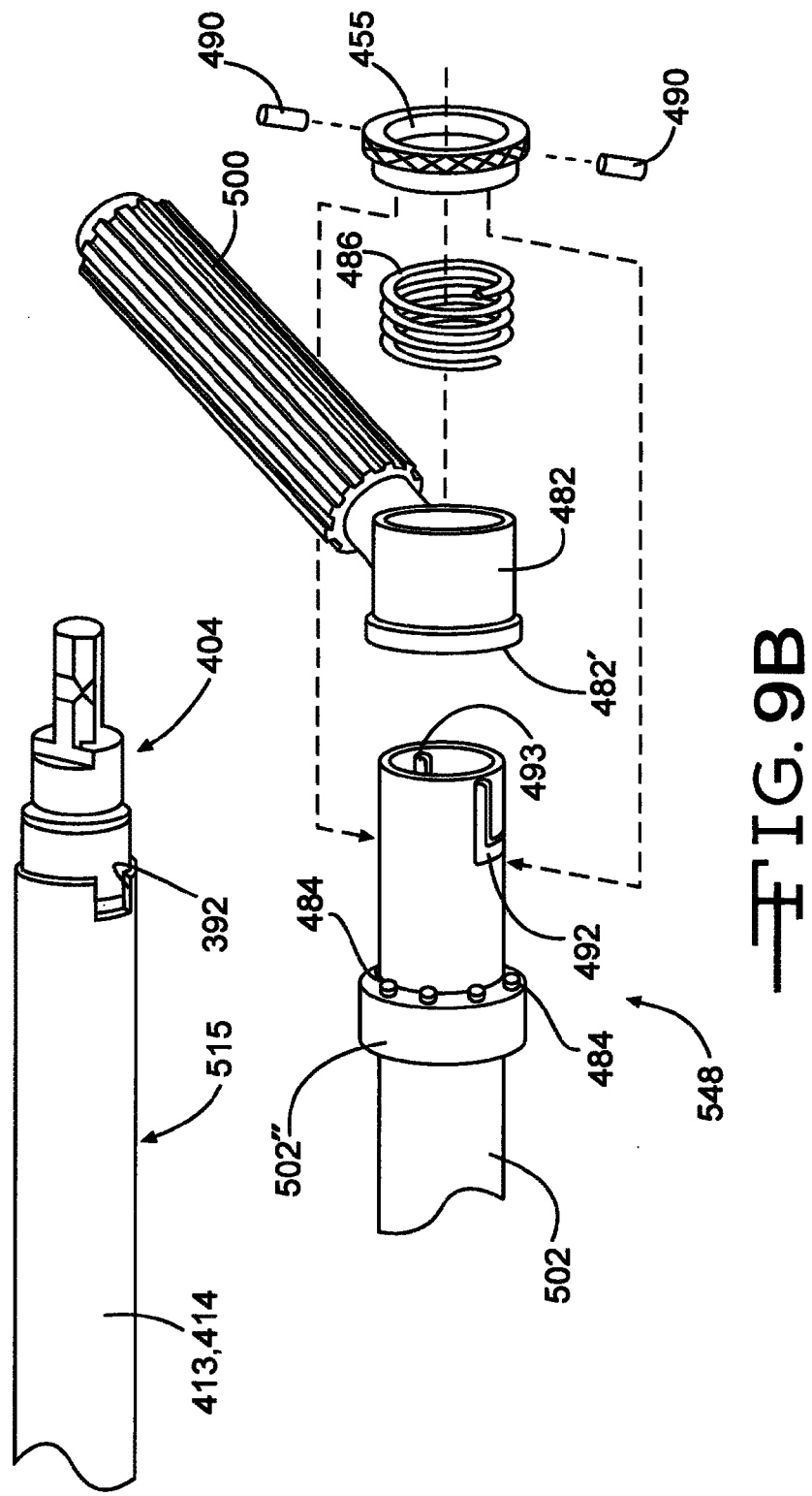
FIG. 9B is a close up of a portion of the exploded view of the alternate embodiment of FIG. 8.

In the embodiment of the reamer spindle 515 illustrated in FIG. 8, the drive end 404 is situated along an axis parallel to, but offset from, the axis 416 of the tool holder fitting 420. Further, as shown in FIGS. 9A and 9B, a repositionable handle 500 doubles as a component of the capture device 450 in order to hold the two housing parts 413 and 414 together. The capture mechanism 447 and capture device 450 slide over the front ends 448 of the housing parts 413 and 414, aligning each with one another and thus encapsulating the drive shaft 507 in order to protect the patient's skin from contacting the torque transmitting shaft 507 after the present device is assembled.

Figure 9C:
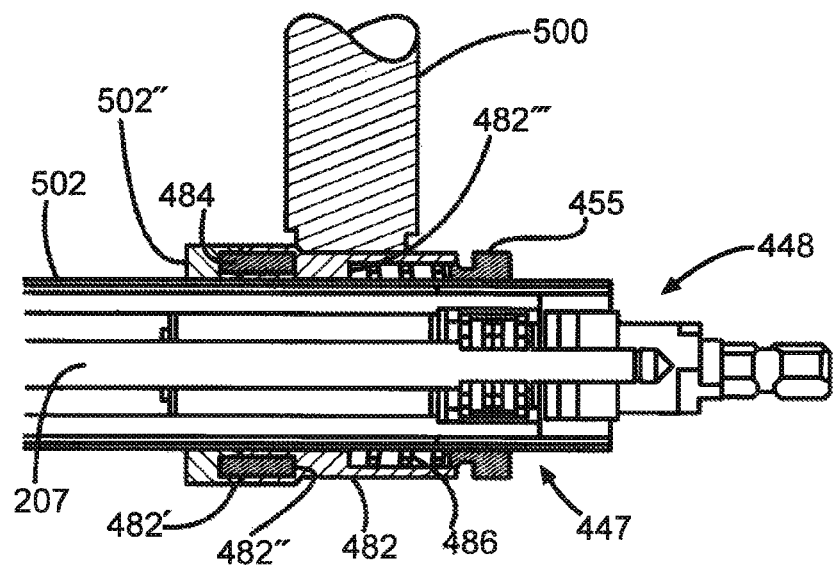
FIG. 9C is a cross-sectional view of the adjustable handle portion of the alternate embodiment of FIG. 8.

FIGS. 9A, 9B and 9C show how the housing parts 413 and 414 are aligned and locked in place in this embodiment of the spindle 515. The housing parts 413 and 414 are oriented with respect to each other when the locking sleeve 502 (having an internal diameter larger than the outside diameter of the assembled housing 413, 414) slides over them and abuts against a bend 480 in the housing parts 413 and 414. Optionally, a facilitating surface may be disposed between the housing parts 413 and 414 and the locking sleeve 502 to facilitate assembly, such as a thin Teflon® coating or sleeves (not shown). A mouth section 502' of the locking sleeve 502 cradles the bend 480 of the assembled housing parts 413 and 414 and prevents rotation of the locking sleeve relative to the housing parts 413 and 414.

The sleeve drive end 548 of the locking sleeve 502 comprises a capture mechanism 447 which connects the housing drive end 448 of the housing parts 413 and 414 to the locking sleeve 502 via a locking device 450. In one embodiment, the locking device 450 had an annular collar 482 onto which a handle 500 was affixed. The collar 482 includes a face 482' having pin recesses 482" into which sleeve pins 484 are receivable. The sleeve pins 484 are fixed to a sleeve shoulder 502" of the locking sleeve 502. The sleeve pins 484 are disposed to be received into the pin recesses 482". The relationship between the sleeve pins 484 and pin recesses is disposed to provide torsionally rigidly to hold the handle 500 in any one of a number of positions (eight in one embodiment) according to the preference of the surgeon. Alternatively, the sleeve shoulder 502" can have fingers or other projections (not shown) that mate with the recesses 482". A collar spring 486 biases the annular collar 482 into engagement with the sleeve pins 484 by a bias against the annular collar 482. In the embodiment illustrated this is accomplished by the collar spring 486 applying spring pressure against an internal shoulder 482''' in the annular collar 482 and against a collar locking ring 455. The collar locking ring 455 includes collar pins 490 which are affixed thereto. The collar pins are received in and extend through sleeve bayonet slots 492 in the drive end 548 of the locking sleeve 502. At least one of the sleeve bayonet slots 492 has a close-end 493 (see FIG. 9B), thus retaining the locking device 450, including the collar ring 455 and bias spring 486, on the drive end 548 of the locking sleeve 502, thus keeping the component part of the capture mechanism 447 together when the spindle 515 is disassembled.

Figure 10:
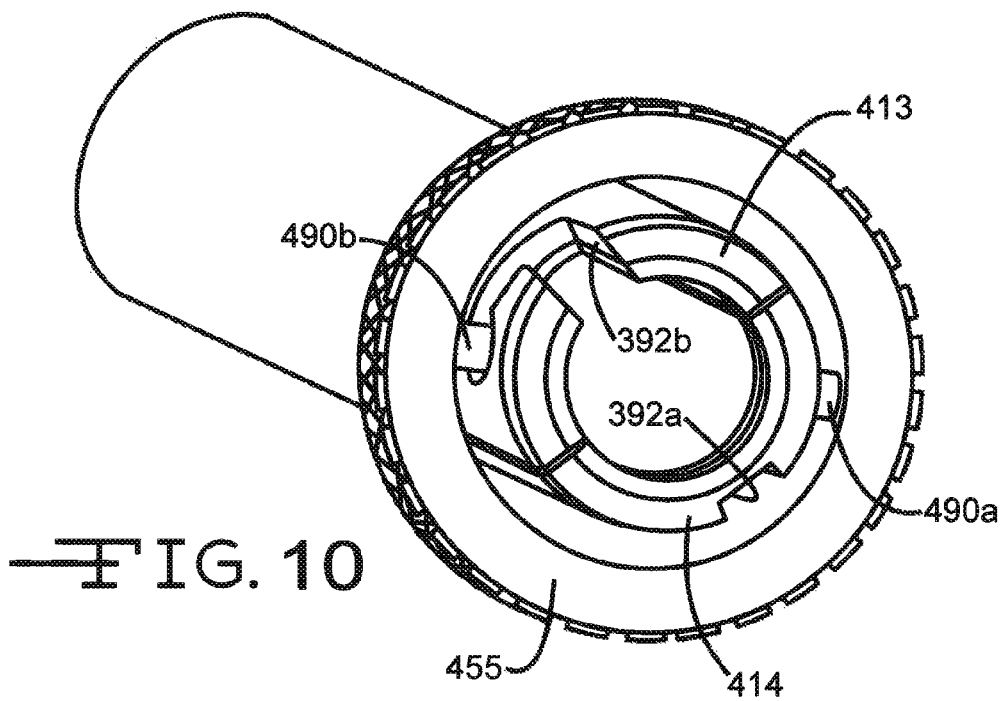
FIG. 10 is a perspective view of key components of the alternate embodiment of FIG. 8.

In order for the locking device 450 to engage and connect to the drive end 448 of the assembled housing parts 413 and 414, the collar pins 490 (490*a* and 490*b*) extend through the sleeve bayonet slots 492 sufficiently to additionally be received in the housing bayonet slots 392 on the assembled housing parts 413 and 414 (see FIG. 10). As shown in FIG. 10, the housing 413, 414 is held together via the collar pins 490 which engage the bayonet slots 392 in each of the housing parts 413 and 414. The illustration in FIG. 10 has the annular sleeve 502, the collar spring 486 and the locking collar 482 removed for clarity.

The collar pins 490 of the collar locking ring 455 and the housing bayonet slots 392 interact with one another to retain the housing parts 413 and 414 in an assembled condition, while concurrently biasing the collar spring 486 so as to engage the annular collar 482 (and thus the handle 500) with the sleeve pins 484. Optionally, the bias force of the collar spring 486 can be selected to enable the surgeon to selectively disengage the collar 482 from the sleeve pins 484 and reposition the angle of the handle 500 relative to the locking sleeve 502 in an alternative position, while avoiding disassembly of the spindle 515.

Figure 9D:
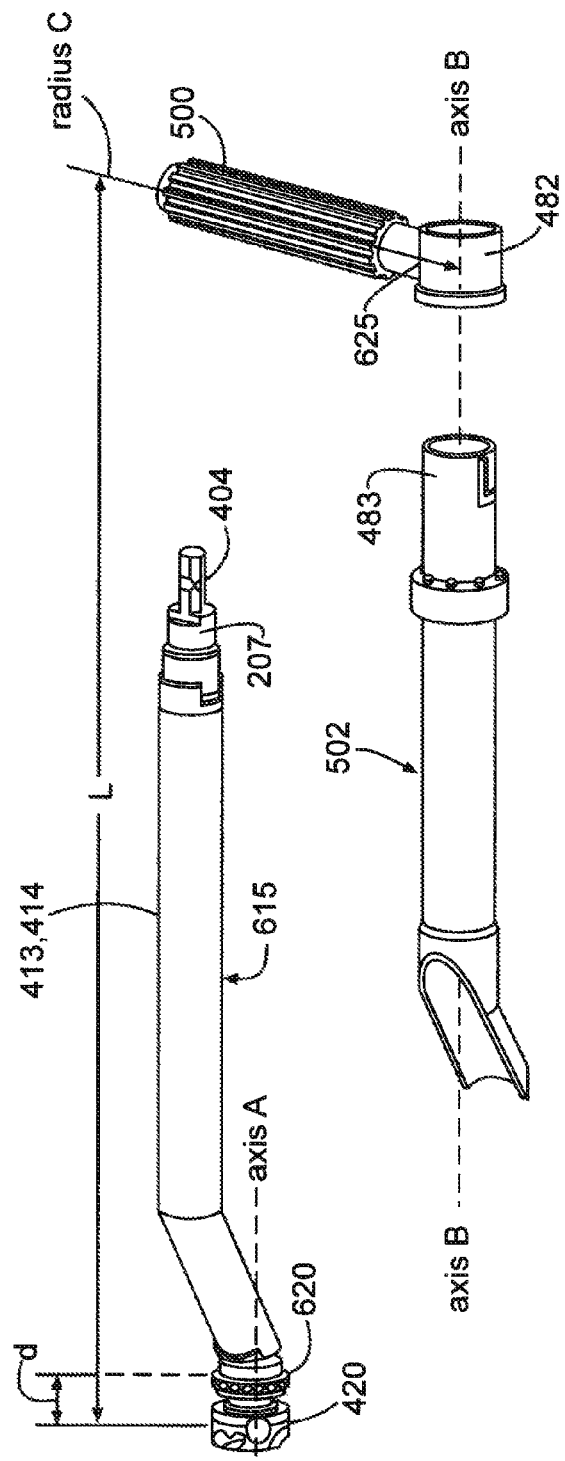
FIG. 9D is a perspective drawing of the principle assemblies of the present invention illustrating their axial, radial and length aspects wherein the precision features of the device reside.

A most important object of the present invention is a precision surgical tool driver which is repeatably assembleable to precise radial, axial and length aspect relationships of its component assemblies. The precision of the device reside in its features which allow it to be disassembled multiple times, and upon each reassembly, the physical dimensions defined by the aspect relationships between its component assemblies are precisely duplicated in the reassembled tool driver. See FIG. 9D an illustration of this. The present precision tool driver comprises three main assemblies and a capture mechanism for precisely interconnecting the main assemblies.

One assembly is a combination spindle housing/drive chain 615. The precision spindle housing 413,414 has an interior disposed to receive and retain the drive train (or drive shaft) 207. The drive chain has a drive attachment end 404 and a tool holder end 420. The drive attachment end 404 is configured to interface with a motive means (not shown) for rotating the drive train 207. Such motive means are known in the field. The tool holder end is configured to connect to a surgical tool head, such tool holder connector configuration being known in the field. The tool holder end 420 of the drive train 207 has an axis of rotation aspect A which is parallel relative to the tool end 620 of the spindle housing 413, 414 from which it extends. The precision of the axis of rotation aspect A is defined by the relationship between the spindle housing 413,414 and the drive train 207 at the tool holder end 420 of the drive train. More specifically, this relationship is defined by the high precision of the bearing or bushing interface between the spindle housing 413, 414 and the drive train 207 at the tool end 620 of the housing. This relationship is such that the spindle tool end 620 and the tool holder end 420 are always substantially coaxial along the axis of rotation A when the drive train 207 and the spindle housing 413, 414 are assembled. The tool holder end 420 also has an axial displacement aspect d relative to the tool end 620 of the spindle sleeve. The axial displacement aspect d is the distance between an end point 620 on the spindle housing 413, 414 and the tool holder end 420. The precision of the axial displacement aspect d is defined by the relationship between the spindle housing and the drive train at the tool holder end of the drive train, which aspect is substantially always the same when the drive train 207 and the housing 413, 414 are assembled.

Another assembly is the precision filled locking sleeve which closely receives the spindle housing and drive train combination 615. In the embodiment illustrated, the drive end 404 of the spindle housing/drive train assembly 615 slides into and is closely received by the locking sleeve 502. The locking sleeve 502 has a sleeve axis B. The locking sleeve 502 is configured to precisely receive and retain the spindle housing 413, 414 so that the sleeve axis B is parallel to the axis of rotation aspect A of the tool holder end 420 of the drive train 207. The locking sleeve 502 also has a mating means 502 which interfaces with the spindle housing 413, 414 to precisely fix the radial aspect of the locking sleeve 502 relative to the spindle housing 413, 414 upon receipt of the spindle housing by the locking sleeve. This is to say, the mating means 502' assures the spindle housing 413, 414 is repeatably receivable in the locking sleeve in the same radial orientation relative to each other. Additionally, in the embodiment illustrated, the mating means 502' provides a precise travel limit on how far the locking sleeve 502 can slide along the spindle housing 413, 414.

The third assembly noted above is the precision locking device 450, which is retained on the locking sleeve 502. The locking device 450 comprises an annular collar 482 slidable on the drive end 483 of the locking sleeve 502 between a sleeve shoulder 502" and a collar ring 455. The collar ring 455 retains the collar 482 on the locking sleeve 502, and incorporates features of a precision bayonet connection, further described elsewhere herein. The collar 482 has a handle 500 attached to it, a collar axis B' through its centerline and a point of attachment 625 of the handle 500 to the collar 482. The collar axis B' is substantially collinear with the sleeve axis B, and in the embodiment illustrated, is coaxial. The point of attachment 625 is disposed along a selected radius C of the collar axis. The collar ring 455 is releaseably engageable to bias/hold the collar 482 against the sleeve shoulder 502" at a precision radial interface 484 and 482', a first part 484 of which is on the sleeve shoulder 502" and the second part 482' being on the annular collar 482. The precision radial interface precisely fixes the radial aspect relationship between the point of attachment and the collar axis radius. In the embodiment illustrated, the radial aspect relationship between the point of attachment of the collar axis to the locking sleeve axis B.

Figure 11C:
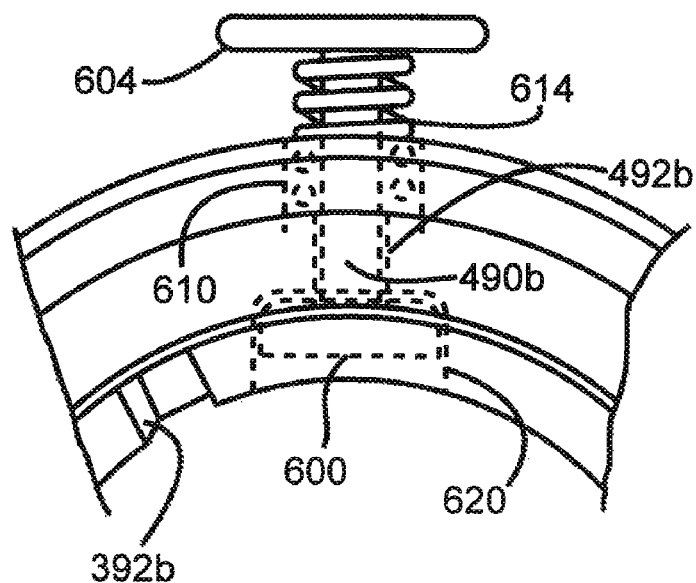
FIG. 11C is an alternative embodiment of the fitted bayonet pin and seat features of the limited-play interconnection of FIGS. 11A and 11B.

FIGS. 11A-11C and 12 illustrate the "limited-play" features of the capture mechanism 447, which connects the housing drive end 448 of the housing 413, 414 to the locking sleeve 502 via the locking device 450. FIGS. 11A and 11B are end-on views of the drive ends of the spindle housing and the locking sleeve assembly, with the fitted bayonet pin disengaged from its seat 620 (in FIG. 11A), and engaged in its seat 620 (in FIG. 11B). In the embodiment shown in FIG. 11A, to engage the housing 413, 414, locking device 450 of the capture mechanism 447 has two collar pins 490a and 490b held by the collar ring 455. One is a fixed collar pin 490a and the other is an extendable collar pin 490b. The extendable collar pin 490b has a fitted bayonet pin head 600 at the end of the collar pin 490b disposed in the interior of the collar ring 455, and a push-button cap 604 at the other end of the collar pin 490b disposed anterior to the collar ring 455 and a pin spring 614 disposed about the shaft of the pin 612. The extendable collar pin 490b is slideably received in a pin passage 610 in the collar ring 455. In the embodiment shown, the pin passage 610 also serves a spring chamber for receiving the pin spring 614. The pin spring 614 provides a biasing force against the push-button cap 604 and the collar ring 455, which normally displaces the push-button cap 604 away from the collar ring 455.

The collar pins 490a and 490b are received in and extend through sleeve bayonet slots 492a and 492b in the drive end 548 of the locking sleeve 502 (also see FIG. 10). The collar pins 490a and 490b extend through their respective sleeve bayonet slots 492a and 492b sufficiently to be received in their respective housing bayonet slots 392a and 392b on the assembled housing parts 413, 414 (also see FIG. 10). The fitted bayonet slot 390b for receiving the fitted bayonet pin 490b includes a head seat 620. The head seat 620 is disposed to closely receive and securely engage the bayonet pin head 600 of the fitted bayonet pin 290b under the bias force of the pin spring 614. The relationship of the configuration of the pin head 600 and the head seal 620 is disposed to enable the close and securely engagement of the pin head in the head seat. This may be accomplished by any of a number of means known to the ordinary skilled artisan for practice in the present invention, including chamfering or beveling the surface of the head seat 620 to closely receive a complementary surface of the pin head 600.

As shown in FIG. 11B, the housing parts 413 and 414 are held together via the collar pins 490a and 490b which engage their respective bayonet slots 392a and 392b in each of the housing parts 413 and 414. The collar pins 490a and 490b of the collar locking ring 455 and the housing bayonet slots 392a and 392b interact with one another to retain the housing parts 413 and 414 in an assembled condition. Thus, the locking device 450 can engage and connect to the drive end 448 of the assembled housing parts 413 and 414. When the depicted embodiment of the present invention is in its assembled condition, as in FIG. 11B, depressing the push-button cap 604 to overcome the bias force causes the pin head 600 to be disengaged from the head seat 620 and to extend beyond the bayonet slot 392b. While the push-button cap is so depressed, the bayonet connection of the locking device 450 can be disengaged in a conventional manner, and the spindle housing 413, 414 can be separated from the capture mechanism 447.

FIG. 11C is an alternative embodiment of the fitted bayonet pin and seat features of the limited-play interconnection of FIGS. 11A and 11B. In this embodiment, head seat 620a comprises both the spindle housing 413, 414 and the locking sleeve 502. This configuration of the pin head seat 620a allows the pin head 600 to be closely receive by and securely engaged with both the spindle housing 413, 414 and the locking sleeve 502, to reduce further the possibility of play in the interconnection between the two assemblies.

Its form helps it to lodge itself in the diameter cut at the end of one of the J-slots in the external locking sleeve. This cut diameter is identical to the largest diameter of the mobile pin. The path of the J-slot outside of this specific diameter is sized according to the smaller diameter of the mobile pin. The pin then slides the length of the J-slot and clicks into the diameter cut at the end of one of the J-slots in the external locking sleeve. The corresponding slot in the internal Z-sleeve must be cut in order that the large diameter of the mobile pin can slide the entire length of the external J-slot. This slot is in fact an L-slot of which the diameter is that of the larger diameter of the fixed pin.

Figure 12:
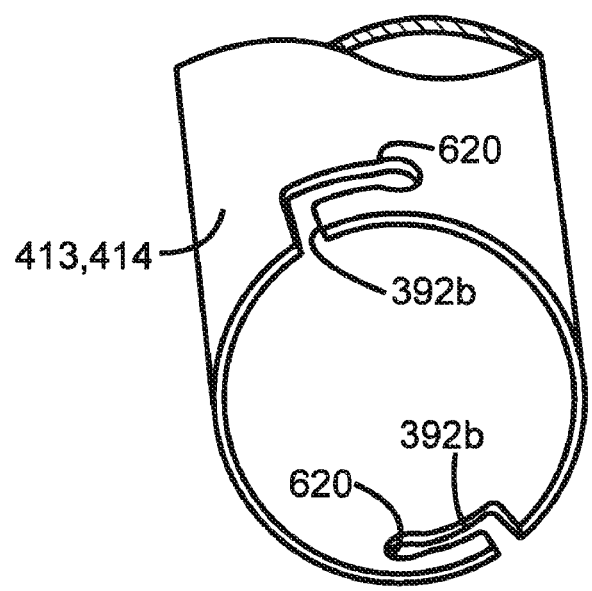
FIG. 12 is a perspective end view of the spindle housing showing the bayonet pin J-slots, one of which includes a close tolerance, fitted bayonet pin seat.

FIG. 12 is a perspective end view of the spindle housing 413, 414 showing the bayonet J-slots 392a and 392b. In some of the embodiments illustrated, one of the two bayonet slots 390 includes a close tolerance, fitted bayonet pin seat 620. However, as known to the ordinary skilled artisan, more than two bayonet slots may be practiced in the present invention. Additionally, as shown in FIG. 12, there may be multiple bayonet slots 392b, each having a close tolerance, fitted bayonet pin seat 620. FIGS. 13A and 13B are instructional illustrations of a manner in which the locking device can be operated to engage (FIG. 13A) or to disengage (FIG. 13B) the drive end of the spindle housing.

Figure 14:
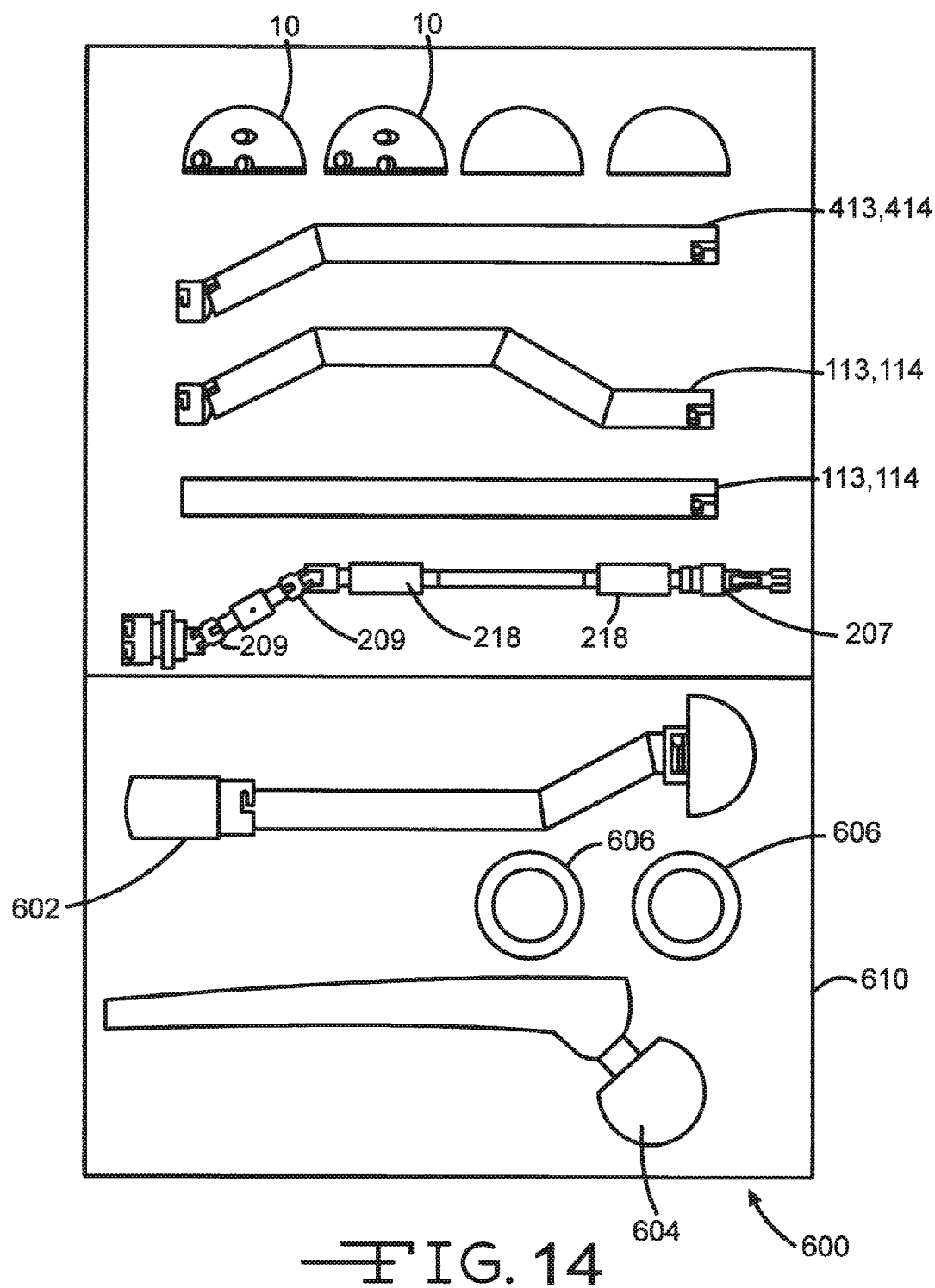
FIG. 14 is a plan view of a surgical reamer kit of the invention.

Referring now to FIG. 14, collectively, these different types of housing parts 213-214, 313-314, and 413-414 can be provided as a kit 600 having a selection of different sized reamer housings 113, tool heads 10, an impactor 602, acetabular implants (not shown), femoral hip prostheses 604, and acetabular cup prostheses 606, the selection of different reamer housing configurations allowing the surgeon to select between a bent, offset configuration or a straight configuration of the reamer spindle depending on the surgeons approach, which may vary during the same operation of between different patients.

While the above description contains many specifics, these should not be construed as limitations on the scope of the invention, but rather as exemplifications of one or another preferred embodiment thereof. Other variations are possible, which would be obvious to one skilled in the art. Accordingly, the scope of the invention should be determined by the scope of the appended claims and their equivalents, and not just by the embodiments.

The claimed invention is:

1. A surgical tool handle, which comprises:
   a) a housing extending along a first longitudinal axis from a proximal housing portion to a housing bend portion deviating from the first longitudinal axis thereof to a distal housing portion, wherein the housing comprises first and second housing parts;
   b) a drive shaft at least partially housed inside the housing comprising the first and second housing parts contacting each other to contain the drive shaft, the drive shaft comprising a driven end fitting located adjacent to the proximal housing portion and being adapted for attachment to a rotary drive source, and a driving end tool holder located adjacent to the distal housing portion and being adapted for selectively engaging and disengaging a surgical tool;
   c) a locking sleeve comprising a sleeve sidewall extending from a proximal sleeve portion having a proximal sleeve end to a distal mouth portion, wherein the locking sleeve encloses the housing from the proximal housing portion to the sleeve mouth portion cradling the housing bend portion to prevent rotation of the first and second housing parts relative to the locking sleeve and wherein the locking sleeve includes at least one locking sleeve bayonet slot through the sleeve sidewall and spaced distally from the proximal sleeve end;
   d) a sleeve shoulder supported on the locking sleeve at an intermediate location between the locking sleeve bayonet slot and the distal mouth portion, wherein a proximal face of the sleeve shoulder includes at least one axial pin having a pin axis spaced from but parallel to the first longitudinal axis of the housing;
   e) a collar supported on the locking sleeve in an axially and rotatably movable relationship, wherein the collar has a distal face with at least two recesses, each having a recess axis spaced from but parallel to the first longitudinal axis;
   f) a handle extending radially outwardly from the collar, wherein the handle is repositionable in a plurality of radially extending orientations with respect to the first longitudinal axis when the axial pin is mated with one of the recesses;
   g) a proximal locking ring supported on the sleeve, wherein the proximal locking ring has at least one proximal locking ring pin aligned perpendicular to the first longitudinal axis and sized to travel along the at least one locking sleeve bayonet slot in the locking sleeve sidewall;
   h) a first spring supported on the locking sleeve to bias between the sleeve shoulder and the proximal locking ring;
   i) wherein with the housing received in the locking sleeve having the sleeve mouth portion cradling the housing bend portion, the proximal locking ring is manipulatable to move the proximal locking ring pin along the locking sleeve bayonet slot against the first spring to a distal slot portion to cause the first spring to bias the axial pin into a mated relationship with one of the recesses to thereby retain the handle in a fixed radial orientation and retain the first and second housing parts contacting each other in an enclosing relationship housing the drive train contained therein; and j) wherein the proximal locking ring is manipulatable to cause the proximal locking ring pin to travel along the locking sleeve bayonet slot to relax the biasing force of the first spring against the collar as the proximal locking ring moves in a proximal direction along the sleeve toward the proximal sleeve end to thereby permit both axial and rotatable manipulation of the handle and the collar with respect to the sleeve shoulder to move the at least one axial pin out of its mated relationship with the one recess to thereby permit:

i) repositioning of the handle from a first radial position to a second, different radial position having the axial pin mated with the other recess; and ii) axial movement of the sleeve with respect to the housing to separate them from each other for subsequent separation of the first and second housing parts from their contact relationship so that the drive shaft can be removed from the housing.

2. The surgical tool handle of claim 1 wherein the drive shaft is selected from the group consisting of a nickel titanium drive shaft, a ferrous metal drive shaft, a flexible round wound cable drive shaft, a flat wire wound cable drive shaft, a gear-driven drive shaft, and a drive shaft having shafts connected via universal joints.

3. The surgical tool handle of claim 1 wherein the sleeve shoulder is fixedly supported on the locking sleeve.

4. The surgical tool handle of claim 1 wherein the drive shaft is comprised of a series of linkages interconnected to each other by universal joints with bearing members supported on the linkages.

5. The surgical tool handle of claim 1 wherein the first spring is a coil spring.

6. The surgical tool handle of claim 1 wherein the locking sleeve has two locking sleeve bayonet slots through the sleeve sidewall, the locking sleeve bayonet slots being aligned diametrically opposite each other.

7. The surgical tool handle of claim 6 wherein the proximal locking ring has two proximal locking ring pins oriented perpendicular to the first longitudinal axis and aligned diametrically opposite each other and wherein the proximal locking ring pins are sized to travel along the respective locking sleeve bayonet slots in the locking sleeve sidewall.

8. The surgical tool handle of claim 1 wherein the locking sleeve has two locking sleeve bayonet slots through the sleeve sidewall, the locking sleeve bayonet slots being aligned diametrically opposite each other and wherein the first and second housing parts each comprise proximal housing bayonet slots extending distally from respective proximal ends thereof.

9. The surgical tool handle of claim 8 wherein the proximal locking ring has two proximal locking ring pins oriented perpendicular to the first longitudinal axis and aligned diametrically opposite each other and wherein with the locking sleeve enclosing the housing from the proximal housing portion to the sleeve mouth portion cradling the housing bend portion, the proximal locking ring pins are sized to travel along the respective locking sleeve bayonet slots aligned with the proximal housing bayonet slots provided in the respective first and second housing parts so that the proximal locking ring is manipulatable to move the proximal locking ring pins along both the locking sleeve bayonet slots and the proximal housing bayonet slots to cause the first spring to bias one of the recesses of the collar into a mated relationship with the axial pin of the sleeve shoulder to thereby retain the handle in a fixed radial orientation and to retain the first and second housing parts contacting each other in an enclosing relationship housing the drive shaft contained therein.

10. The surgical tool handle of claim 8 wherein at least one of the proximal locking ring pins has a pin head mounted on a neck portion thereof, and wherein at least one of the housing bayonet slots includes a head seat adapted to engage the pin head, the pin head being wider than one portion of the housing bayonet slot through which one portion the neck portion may pass, wherein further, after the neck portion passes through the one wider portion and the pin is positioned proximate the head seat, the locking pin is biased to engage the pin head in the head seat.

11. The surgical tool handle of claim 10 wherein the pin head is received in the pin seat in a closely spaced relationship.

12. The surgical tool handle of claim 1 wherein the distal face of the collar includes at least four recesses adapted to mate with the at least one axial pin of the sleeve shoulder.

13. The surgical tool handle of claim 12 wherein the proximal face of the sleeve shoulder includes at least two axial pins adapted to mate with the at least four recesses provided in the distal face of the collar.

14. The surgical tool handle of claim 1 wherein the distal housing portion extends along a second longitudinal axis spaced from, but parallel to the first longitudinal axis of the proximal housing portion.

15. The surgical tool handle of claim 14 wherein at least one of the first and second housing parts comprise a distal bayonet slot at the distal housing portion and wherein the drive shaft comprises a distal locking ring having at least one distal locking ring pin aligned perpendicular to the second longitudinal axis and sized to travel along the at least one distal bayonet slot in the one of the first and second housing parts and wherein the distal locking ring is manipulatable to move the distal locking ring pin proximally along the distal housing bayonet slot into an engaged position to retain the first and second housing parts contacting each other in an enclosing relationship housing the drive shaft contained therein and alternatively to move the distal locking ring pin distally along the distal housing bayonet slot into a disengaged position to permit separation of the housing parts from their contact relationship so that the drive shaft can be removed from the housing.

16. The surgical tool handle of claim 1 wherein the first and second housing parts each comprise distal housing bayonet slots extending distally from respective distal ends thereof.

17. The surgical tool handle of claim 16 wherein the distal locking ring has two distal locking ring pins oriented perpendicular to the second longitudinal axis and aligned diametrically opposite each other and wherein the distal locking ring pins are sized to travel along the distal housing bayonet slots provided in the respective first and second housing parts so that the distal locking ring is manipulatable to move the distal locking ring pins proximally along the distal housing bayonet slots into an engaged position to retain the first and second housing parts contacting each other in an enclosing relationship housing the drive shaft contained therein and alternatively to move the distal locking ring pins distally along the distal housing bayonet slots into a disengaged position to permit separation of the housing parts from their contact relationship so that the drive shaft can be removed from the housing.

18. The surgical tool handle of claim 1 wherein the driving end tool holder comprises a slide carrying a pin that cooperates with the catch of a head to secure a first reamer to the drive shaft and wherein the catch is manipulatable to move the slide pin with respect to the catch to permit removal of the first reamer from the drive shaft and replacement with a second reamer.

19. The surgical tool handle of claim 1 wherein a handle extends outwardly from the locking sleeve.

20. A surgical tool handle, which comprises:
  a) a housing extending along a longitudinal axis from a proximal housing portion to a housing bend portion deviating from the longitudinal axis thereof to a distal housing portion, wherein the housing comprises first and second housing parts;
  b) a drive shaft at least partially housed inside the housing comprising the first and second housing parts contacting each other to contain the drive shaft, the drive shaft comprising a driven end fitting located adjacent to the proximal housing portion and being adapted for attachment to a rotary drive source, and a driving end tool holder located adjacent to the distal housing portion and being adapted for selectively engaging and disengaging a surgical tool;
  c) a locking sleeve comprising a sleeve sidewall extending from a proximal sleeve portion having a proximal sleeve end to a distal mouth portion, wherein the locking sleeve encloses the housing from the proximal housing portion to the sleeve mouth portion cradling the housing bend portion to prevent rotation of the first and second housing parts relative to the locking sleeve and wherein the locking sleeve includes at least one locking sleeve bayonet slot in the sleeve sidewall and spaced distally from the proximal sleeve end;
  d) a proximal locking ring supported on the locking sleeve, wherein the proximal locking ring has at least one proximal locking ring pin aligned perpendicular to the longitudinal axis and sized to travel along the at least one locking sleeve bayonet slot in the locking sleeve sidewall;
  e) wherein with the housing received in the locking sleeve having the sleeve mouth portion cradling the housing bend portion, the proximal locking ring is manipulatable to move the proximal locking ring pin along the locking sleeve bayonet slot to a distal slot portion to retain the first and second housing parts contacting each other in an enclosing relationship housing the drive train contained therein; and
  f) wherein the proximal locking ring is manipulatable to cause the proximal locking ring pin to travel along the locking sleeve bayonet slot to disengage therefrom and thereby permit axial movement of the locking sleeve with respect to the housing to separate them from each other for subsequent separation of the first and second housing parts from their contact relationship so that the drive shaft can be removed from the housing.

21. A surgical tool handle, which comprises:
  a) a housing extending from a proximal housing portion to a distal housing portion, wherein the housing comprises first and second housing parts;
  b) a drive shaft at least partially housed inside the housing comprising the first and second housing parts contacting each other to contain the drive shaft, the drive shaft comprising a driven end fitting located adjacent to the proximal housing portion and being adapted for attachment to a rotary drive source, and a driving end tool holder located adjacent to the distal housing portion and being adapted for selectively engaging and disengaging a surgical tool;
  c) a locking sleeve comprising a sleeve sidewall extending from a proximal sleeve portion having a proximal sleeve end to a distal sleeve portion, wherein the locking sleeve includes at least one locking sleeve bayonet slot in the sleeve sidewall and spaced distally from the proximal sleeve end;
  d) a handle connected to and extending outwardly from the locking sleeve;
  e) a proximal locking ring supported on the locking sleeve, wherein the proximal locking ring has at least one proximal locking ring pin aligned perpendicular to a longitudinal axis of the housing and sized to travel along the at least one locking sleeve bayonet slot in the locking sleeve sidewall;
  f) wherein with the housing received in the locking sleeve, the proximal locking ring is manipulatable to move the proximal locking ring pin along the locking sleeve bayonet slot to a distal slot portion to retain the first and second housing parts contacting each other in an enclosing relationship housing the drive train contained therein; and
  g) wherein the proximal locking ring is manipulatable to cause the proximal locking ring pin to travel along the locking sleeve bayonet slot to disengage therefrom and thereby permit axial movement of the locking sleeve with respect to the housing to separate them from each other for subsequent separation of the first and second housing parts from their contact relationship so that the drive shaft can be removed from the housing.

22. The surgical tool handle of claim 21 wherein the housing extends along a longitudinal axis from the proximal housing portion to a housing bend portion deviating from the longitudinal axis thereof to the distal housing portion and wherein the locking sleeve encloses the housing from the proximal housing portion to a sleeve mouth at the distal sleeve portion that cradles the housing bend portion to prevent rotation of the first and second housing parts relative to the locking sleeve.

23. The surgical tool handle of claim 21 wherein the handle extends radially outwardly from the locking sleeve with respect to a longitudinal axis of the housing.

24. The surgical tool handle of claim 21 wherein at least one of the proximal locking ring pins has a pin head mounted on a neck portion thereof, and wherein at least one of the housing bayonet slot includes a head seat adapted to engage the pin head, the pin head being wider than one portion of the housing bayonet slot through which one portion the neck portion may pass, wherein further, after the neck portion passes through the one wider portion and the pin is positioned proximate the head seat, the locking pin is biased to engage the pin head in the head seat.

25. The surgical tool handle of claim 24 wherein the pin head is received in the pin seat in a closely spaced relationship.

* * * * *

UNITED STATES PATENT AND TRADEMARK OFFICE
CERTIFICATE OF CORRECTION

| | | Page 1 of 1 |
|---|---|---|
| PATENT NO. | : 7,749,227 B2 | |
| APPLICATION NO. | : 11/536792 | |
| DATED | : July 6, 2010 | |
| INVENTOR(S) | : Lechot | |

It is certified that error appears in the above-identified patent and that said Letters Patent is hereby corrected as shown below:

Cover Page add the following:

-- (63) Continuation-in-part of PCT application No. PCT/IB03/01725, filed 28 Apr. 2003. --

Cover Page add the following:

item -- [60] Provisional application No. 60/765,692, filed on February 6, 2006. --

Column 1 delete the paragraph spanning lines 8-12:

"The present application claims the benefit of prior filed U.S. Provisional Patent Application Ser. No. 60/765,692 filed 6 Feb. 2006, to which the present application is a regular U.S. national application, and of prior PCT application No. PCT/IB03/01725, filed 28 Apr. 2003."

Column 1 line 8 insert the following paragraph:

-- This application claims the benefit of U.S. Provisional Patent Application Ser. No. 60/765,692 filed 6 Feb. 2006, and this application is a continuation-in-part of PCT application No. PCT/IB03/01725, filed 28 Apr. 2003. --

Signed and Sealed this
Twenty-sixth Day of March, 2013

Teresa Stanek Rea
*Acting Director of the United States Patent and Trademark Office*